US012636332B2

(12) United States Patent
Hayashi et al.

(10) Patent No.: US 12,636,332 B2
(45) Date of Patent: May 26, 2026

(54) METHOD OF IMPROVING REPRODUCTIVE ABILITY

(71) Applicant: Osato International Inc., Gifu (JP)

(72) Inventors: Yukiyasu Hayashi, Gifu (JP); Stefano Fais, Rome (IT); Mariantonia Logozzi, Rome (IT)

(73) Assignee: Osato International Inc., Gifu (JP)

( * ) Notice: Subject to any disclaimer, the term of this patent is extended or adjusted under 35 U.S.C. 154(b) by 822 days.

(21) Appl. No.: 17/760,834

(22) PCT Filed: Sep. 16, 2020

(86) PCT No.: PCT/JP2020/035121
§ 371 (c)(1),
(2) Date: Mar. 16, 2022

(87) PCT Pub. No.: WO2021/054373
PCT Pub. Date: Mar. 25, 2021

(65) Prior Publication Data
US 2022/0347248 A1 Nov. 3, 2022

(30) Foreign Application Priority Data
Sep. 20, 2019 (JP) ................................. 2019-171916

(51) Int. Cl.
*A61K 36/185* (2006.01)
*A61K 35/48* (2015.01)
*A61P 43/00* (2006.01)
(52) U.S. Cl.
CPC ............ *A61K 36/185* (2013.01); *A61K 35/48* (2013.01); *A61P 43/00* (2018.01); *A61K 2236/19* (2013.01)
(58) Field of Classification Search
CPC ...... A23L 19/00; A61P 43/00; A61K 2236/19
See application file for complete search history.

(56) References Cited

U.S. PATENT DOCUMENTS

| | | | | |
|---|---|---|---|---|
| 10,993,980 B2 * | 5/2021 | Hayashi | ............... | A61K 36/185 |
| 2007/0264372 A1 * | 11/2007 | Sala | ......................... | A61P 17/02 424/777 |
| 2016/0184377 A1 * | 6/2016 | Hayashi | .................... | A61P 3/10 424/278.1 |

FOREIGN PATENT DOCUMENTS

| | | |
|---|---|---|
| JP | 2006-075086 A | 3/2006 |
| JP | 2011-041478 A | 3/2011 |
| WO | 2016/027333 A1 | 2/2016 |
| WO | 2016/027334 A1 | 2/2016 |
| WO | 2016/093104 A1 | 6/2016 |

OTHER PUBLICATIONS

Schellnegger et al (Frontiers in Aging, Jan. 2024, vol. 5, pp. 1-11) (Year: 2024).*
Logozzi et al (Antioxidants, Feb. 2020, vol. 9, pp. 1-17) (Year: 2020).*
Philippe et al (Functional Foods in Health and Disease, Feb. 2018, vol. 8, pp. 122-144) (Year: 2018).*
Danese et al (La Clinica Terapeutica, 2006, vol. 157, pp. 195-198) (Year: 2006).*
Buffa et al (The Journal of Nutrition, Health and Aging, 2010, vol. 14, pp. 97-102) (Year: 2010).*
Newswire (Fertility Issues with Diabetes and Men and Women, Jun. 15, 2015, https://www.newswire.com/news/fertility-issues-with-diabetes-in-men-and-women) (Year: 2015).*
Diabetes UK (Nearly 7000 Children and Young Adults With Type 2 Diabetes, Nov. 22, 2018, https://www.diabetes.org.uk/about-us/news/children-young-adults-type-2-rise) (Year: 2018).*
International Preliminary Report on Patentability and Written Opinion issued in corresponding International Patent Application No. PCT/JP2020/035121 dated Mar. 31, 2022.
International Search Report issued in corresponding International Patent Application No. PCT/JP2020/035121 dated Dec. 1, 2020.
Aruoma et al., "Applications and bioefficacy of the functional food supplement fermented papaya preparation," Toxicology, 278 (1): 6-16 (2010).
Aruoma et al., "Diabetes as a risk factor to cancer: Functional role of fermented papaya preparation as phytonutraceutical adjunct in the treatment of diabetes and cancer," Mutation Research, 768: 60-68 (2014).
Logozzi et al., "Oral Administration of Fermented Papaya (FPP(R)) Controls the Growth of a Murine Melanoma through the In Vivo Induction of a Natural Antioxidant Response," Cancers, 11: 118 (2019).
Liu et al., "Oxidative stress contributes to arsenic-induced telomere attrition, chromosome instability, and apoptosis," Journal of Biological Chemistry, 278 (34): 31998-32004 (2003).
Ishikawa, "Cellular senescence and Chromosome telomere", Japanese Journal of Geriatrics, 37,: 1, p. 19-25 (2000). (see partial English translation).
Logozzi et al., "Anti-aging and anti-tumor effect of FPP supplementation,", European Journal of Translational Myology, 30 (1): 58-61 (2020).
Logozzi et al., "Beneficial Effects of Fermented Papaya Preparation (FPP) Supplementation on Redox Balance and Aging in a Mouse Model", Antioxidants, 9: 144 (2020).
Santini et al., "Nutraceuticals-shedding light on the grey area between pharmaceuticals and food," Expert Review of Clinical Pharmacology, 11 (6): 545-547 (2018).

* cited by examiner

*Primary Examiner* — Mark V Stevens
(74) *Attorney, Agent, or Firm* — Morgan, Lewis & Bockius LLP

(57) ABSTRACT

An object of the present invention is to provide a novel use of fermented papaya preparation. A composition of the present invention is a composition for elongating telomeres comprising fermented papaya preparation as an active ingredient.

18 Claims, 9 Drawing Sheets

(A)

(B)

(A)

(B)

MEASUREMENT RESULT OF TELOMERASE ACTIVITY BY ELISA

MEASUREMENT RESULT OF ANTIOXIDATION ABILITY BY PAO (A)

(B)

(A)

(B)

METHOD OF IMPROVING REPRODUCTIVE ABILITY

TECHNICAL FIELD

The present invention relates to a composition for elongating telomeres comprising fermented papaya preparation as an active ingredient.

BACKGROUND ART

Fermented papaya preparation (FPP) produced by fermenting immature fruits of *Carica papaya* Linn with sugar and edible yeast fungi increases maltose and maltotriose by mixing the fermented papaya preparation with saliva as compared with mixing the fermented papaya preparation with water.

Oligosaccharides increase by the oral ingestion of FPP, and a function for controlling the intestinal environment is expected, and the suppression of blood sugar level increase and the energy metabolism improvement of type II diabetes patients, and the wound healing promotion due to immunity enhancement are also expected (Patent Literatures 1 to 3). It is known that FPP also has an antioxidation characteristic, and an effect on various symptoms accompanying aging is obtained (Non Patent Literature 1).

It has been reported that FPP is rich in amino acids and glucide, influences the immune system, promotes the production of good reactive oxygen species (ROSs), eliminates bad ROSs and acts as an antioxidant, besides, FPP can improve the "respiratory burst" function of II type diabetes patients (Patent Literatures 4 and 5). It has also been reported that FPP especially acts on angiogenic response subsequently to the response of macrophages in wounds to improve the result of diabetic wounds (Non Patent Literature 2).

The present inventors have investigated the effect of the oral ingestion of FPP (registered trademark, Osato Research Institute) in the prevention and treatment of melanoma using a normal immunocompetent mouse model (C57BL/6J) inoculated with B16 melanoma cells and consequently found that FPP controls tumor sizes, and this corresponds with a decrease in the blood ROS level and increase in the plasma levels of natural antioxidants (GSH and SOD-1) (Non Patent Literature 3). No metastasis occurred in any of the mice which ingested FPP. The result of Non Patent Literature 3 strongly suggests the probability that FPP can activate the natural antioxidation system of the living body to consequently contribute to the prevention and suppression of tumor proliferation.

CITATION LIST

Patent Literature

Patent Literature 1: Japanese Unexamined Patent Publication No. 2011-041478

Patent Literature 2: International Publication No. WO 2016-027334

Patent Literature 3: International Publication No. WO 2016-027333

Patent Literature 4: International Publication No. WO 2016-027334

Non Patent Literature

Non Patent Literature 1: Aruoma O. I. et al., Applications and bioefficacy of the functional food supplement fermented papaya preparation. Toxicology 278: 6-16, 2010.

Non Patent Literature 2: Aruoma O. I. et al., Diabetes as a risk factor to cancer: Functional role of fermented papaya preparation as phytonutraceutical adjunct in the treatment of diabetes and cancer. Mutat. Res./Fundam. Mol. Mech. Mutagen. 2014, 768, 60-68

Non Patent Literature 3: Logozzi M et al., Oral Administration of Fermented Papaya (FPP) Controls the Growth of a Murine Melanoma through the In Vivo Induction of a Natural Antioxidant Response. Cancers (Basel). 2019 Jan. 20; 11(1)

SUMMARY OF INVENTION

Technical Problem

An object of the present invention is to provide a novel use of fermented papaya preparation.

Solution to Problem

The present inventors have found that the oral administration of FPP to mice results in improvement in the total antioxidation ability and the telomerase activity in plasma and also increase in the telomere lengths of stem cells and reproductive cells.

That is, the present invention relates, for example, to the following inventions.

[1]

A composition for elongating telomeres, comprising fermented papaya preparation as an active ingredient.

[2]

The composition according to [1], wherein the composition suppresses telomere shortening due to aging.

[3]

The composition according to [1] or [2], wherein the composition improves telomerase activity.

[4]

The composition according to [3], wherein the composition improves telomerase activity in reproductive cells or stem cells.

[5]

The composition according to any one of [1] to [4], wherein the composition suppresses cell aging.

[6]

The composition according to [5], wherein the composition suppresses individual aging.

[7]

The composition according to any one of [1] to [6], wherein the composition is a pharmaceutical composition or a food composition.

[8]

The composition according to any one of [1] to [7], wherein a dosage of the fermented papaya preparation is 0.5 to 30 g/day with respect to an adult having a body weight of 70 kg.

[9]

A method for elongating telomeres, comprising administering an effective dose of fermented papaya preparation to a patient in need thereof.

[10]

The method of [9], wherein the method suppresses telomere shortening due to aging.

[11]

The method of [9], wherein the method improves telomerase activity.

3

[12]

The method according to [11], wherein the method improves telomerase activity in reproductive cells or stem cells.

[13]

The method of [9], wherein the method suppresses cell aging.

[14]

The method of [9], wherein the method suppresses individual aging.

[15]

Use of fermented papaya preparation in a food composition or a pharmaceutical composition for elongating telomeres.

Advantageous Effects of Invention

According to the composition of the present invention, telomers can be elongated, an antiaging effect can be expected by daily ingestion.

DESCRIPTION OF EMBODIMENTS

Figure 1:
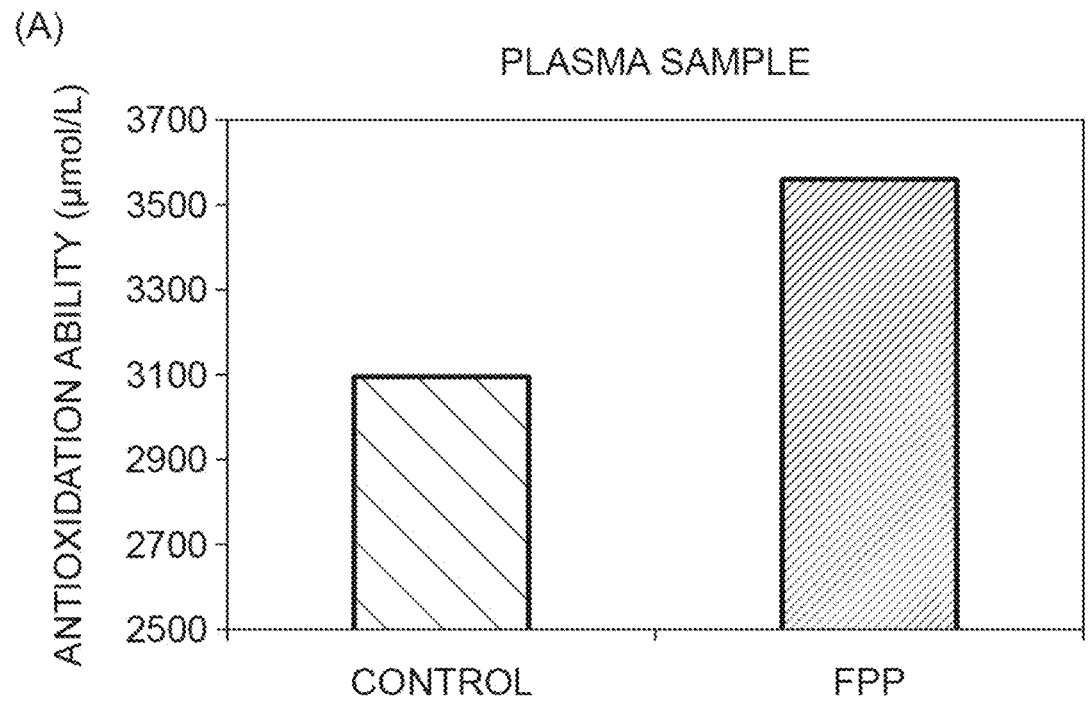
FIG. 1 shows the results of the total antioxidation ability (A) and the telomerase activity (B) in mouse plasma of Example 1.
Figure 1:
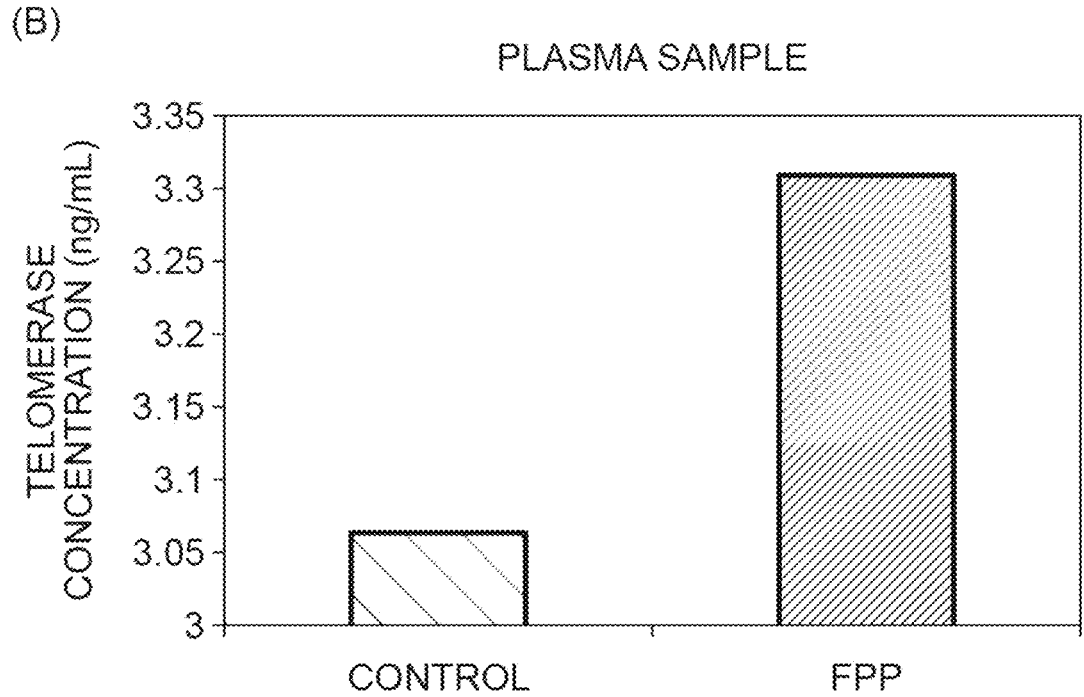

A composition according to the present invention is a composition for elongating telomeres comprising fermented papaya preparation as an active ingredient.

The composition of the present invention contains the fermented papaya preparation (FPP) as the active ingredient. As mentioned above, FPP is a fermented product derived from papaya produced by fermenting immature fruits of *Carica papaya* Linn with sugar and edible yeast fungi.

It is preferable that the FPP be fermented papaya preparation developed by Osato Research Institute, produced by Osato laboratory Inc., and sold by OSATO International, Inc. (Patent Literature 1 and Non Patent Literature 8). The FPP is available as "FPP: Fermented Papaya Preparation"® or "Immun' Âge"®. The FPP is produced in a factory certified in accordance with ISO 9001:2015, ISO 14001: 2015, and ISO 22000:2005 and first certified in accordance with FSSC 22000, which is the strictest food safety standard in Europe and America, by JIA in Japan and guaranteed from the viewpoints of quality, the environment and safety.

A method for producing FPP is described, for example, in Patent Literature 1. As an example, *Carica papaya* Linn grown in Hawaii State is fermented with edible yeast for around 10 months to produce FPP. According to the analysis by Japan Food Research Laboratories, 91.2 g of carbohydrate is contained, and small amounts of protein (0.3 g), lipid (less than 0.1 g), potassium (14.9 mg), and water (8.5 g) are contained besides in 100 g of FPP (Lot No. 091; assay specification on May 27, 2014).

Telomeres have structure consisting of DNAs located at the terminals of chromosomes in eukaryotes and having characteristic repeated sequences (repetitive sequences) and various proteins, and play the role of protecting the chromosome terminals. Telomeres can protect chromosomes from the decomposition or repair of DNA and maintain the physical and genetic stability by the unique structure thereof. Chromosomes lacking in telomeres are recognized as abnormal DNA terminals by cells and decomposed by enzymes, and the terminals of the chromosomes is abnormally fused by the repair mechanism. Such instability of chromosomes cause cell death or oncogenesis. It has been suggested that endothelial cells whose chromosomes are unstable or the cells are unable to divide may induce cerebral and cardiac angiopathy due to aging such as arteriosclerosis, and lifestyle-related diseases.

Telomeres are elongated with telomerase (TE). Telomerase (TE) is an enzyme that adds DNA repetitive sequences to telomeres at chromosome terminals. Every time DNA replicates, telomeres are shortened, and the role of telomerase is however to maintain the integrity thereof. In cells without telomerase, the telomere shortening proceeds by cell divisions, the stop of cell division called the Hayflick limit (limit of the number of times of divisions) occurs, and the cells become in a state called cell aging. Telomerase is not expressed, or has only weak activity in human somatic cells. When human somatic cells are extracted and cultured, telomeres are therefore shortened. It is currently believed that the telomerase activity and the telomere length are molecular characteristics of aging. The activity of telomerase is observed in reproductive cells, stem cells, cancer cells, or the like in humans, and partakes in a property that enables those cells to continue division. Telomerase therefore attracts attention from both aspects of cancer treatment by suppressing the telomerase activity and the prolongation of cell division lives by enhancing the activity.

Although it has been suggested that cell aging due to the telomere shortening causes individual aging, the relationship therebetween is unclarified. The telomere shortening suppression is however expected to lead to the prolongation of cell lives, by extension, the delay of individual aging, and the prolongation of lives. Since cell aging due to the telomere shortening may induce cancer and lifestyle-related diseases, the telomere shortening suppression is expected to lead to the prevention of cancer, cerebral and cardiac angiopathy, and lifestyle-related diseases.

Elongating telomers (the elongation of telomeres) herein includes both increasing the telomere lengths (an increase in the telomere length) and suppressing the shortening of the telomere lengths (telomere shortening). The increase in the telomere lengths includes elongating the telomere lengths by improving the telomerase activity. It has been proved by the below-mentioned in vivo Examples that FPP improves the telomerase activity in reproductive cells and stem cells, and the prolongation of reproductive cell and stem cell lives and the prolongation of reproduction lives (period during which reproduction is feasible) are also estimated.

The telomere shortening includes, for example, decrease in the telomere lengths due to cell divisions; and when the telomere shortening is suppressed, the telomere shortening is restrained, especially the telomere shortening due to aging is suppressed, and the telomere lengths is long as compared with normal cells, in which the telomere shortening is not suppressed. Since the telomere shortening leads to cell aging, the suppression of the telomere shortening enables suppressing cell aging. The cell lives are therefore long as compared with normal cells, in which the telomere shortening is not suppressed. Therefore, individual aging is also suppressed, and individual lives can be prolongated.

The telomere lengths can be measured by a known method. The measurement is feasible, for example, using a Telomere PNA Kit/FITC (Agilent Technologies, Inc., Santa Clara, CA, USA) for flow cytometry, described in Example 3.

The telomerase activity can be measured by a known method. The measurement is feasible, for example, by colorimetric sandwich-ELISA assay using an ELISA kit (Elabscience®, Houston, Tex., USA), described in Example 3.

The composition in the present embodiment may be a pharmaceutical composition or a food composition. As mentioned above, the fermented papaya preparation mainly contains carbohydrate, and contains a small amount of protein besides, and the safety is therefore very high. The amount of the fermented papaya preparation used is therefore not particularly limited, and only has to be, for example, 0.5 to 30 g/day, and is preferably 1 to 20 g/day, further preferably 3 to 15 g/day or 9 to 30 g/day, and the most preferably 3 to 9 g/day, 6 to 9 g/day, or 9 to 15 g/day with respect to an adult having a body weight of 70 kg.

Although the composition in the present invention can be ingested anytime regardless of age, the ingestion during the young age period and the middle age period is more effective from the viewpoint of telomere elongation. It is preferable to start the ingestion, for example, at the age of 13 to 60, 13 to 50, 13 to 40, 13 to 30, 13 to 25, or 13 to 20, and it is preferable to ingest the composition, for example, from the age of 13, 15, 18, or 20. It is preferable from the viewpoint of safety that infants at the age of less than 1, infants at the age of less than 3, or infants at the age of less than 5 ingest the composition based on advice or prescription from doctors or pharmacists. It is preferable from the viewpoint of telomere elongation that the ingestion period be 1 month or more, 2 months or more, 6 months or more, 1 year or more, 3 years or more, 5 years or more, 10 years or more, 15 years or more, 20 years or more, 25 years or more, 30 years or more, 35 years or more, 40 years or more, or 45 years or more.

The fermented papaya preparation can be optionally prepared into various shapes such as granules, powder, and fine granules so as to be suitable for oral ingestion, and contains fermented papaya preparation as an active ingredient, and additives such as a vehicle, a binder, and a lubricant can be optionally added at the time of the preparation Hereinafter, the present invention will be more specifically described based on the Examples. The present invention is however not limited to the following Examples.

EXAMPLES

Example 1

First, 15 mouse models suitable for aging investigation (C57BL/6J, female) were used for each of an ingestion group and a control group. FPP (registered trademark, Osato Research Institute, Japan) dissolved in tap water (3 g FPP/ 500 mL) was given to the ingestion group everyday from 4 weeks after birth for 10 months, and the mice were let to ingest the solution freely. Only tap water is given to the control group. The aqueous FPP solution and the tap water were exchanged for a new solution and new tap water everyday, respectively.

Subsequently, 10 months after the oral ingestion, blood was collected, the mice were slaughtered, and bone marrow from the shinbones and the ovaries were then collected. Experiments for confirming the total antioxidation ability and the telomerase activity in mouse plasma, and the telomere lengths of bone marrow stem cells and ovarian germ cells (reproductive cells) were performed. Plasma was separated from the blood, the plasma samples were measured for the antioxidation abilities using a PAO assay kit, and the plasma samples were measured for the telomerase activities using a telomerase ELISA kit. A physiological saline solution was used for separating stem cells from the bone marrow, a trypsin/EDTA solution was used for separating reproductive cells from the ovaries, and cell suspensions were separately prepared and treated through a cell strainer. The respective unicellular suspensions of the bone marrow and the ovaries were measured for the telomere lengths by flow cytometry analysis (FACS; registered trademark) using a Telomere PNA Kit/FITC. Each of the kits was used according to the instructions.

The measured values of the 15 mice were averaged. The results of the total antioxidation abilities were shown in FIG. 1(A), and the results of the telomerase activities were shown in FIG. 1(B). FIG. 1 has shown that the total antioxidation ability in plasma of the mice that ingested FPP was around twice the total antioxidation ability of the control mice, which did not ingest FPP, and the telomerase activity in plasma of the mice that ingested FPP was around three times the telomerase activity of the control mice, which did not ingest FPP, at the end of the test.

Figure 2:
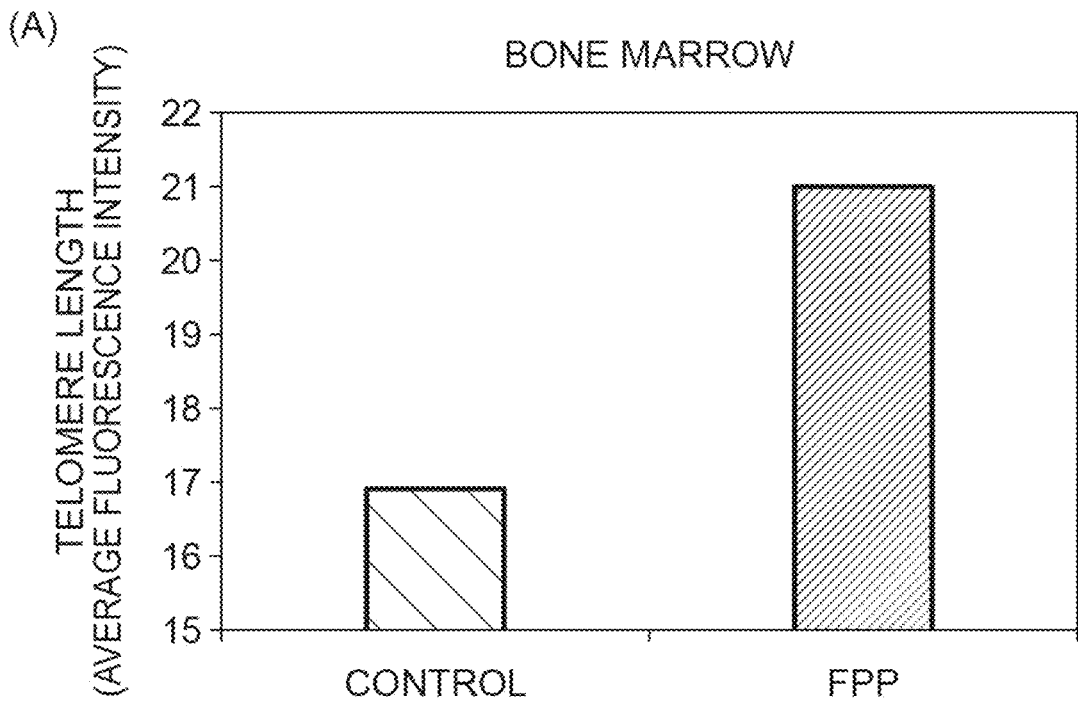
FIG. 2 shows the results obtained by measuring the telomere lengths of cells collected from mouse bone marrow (A) and the ovaries (B) of Example 1.
Figure 2:
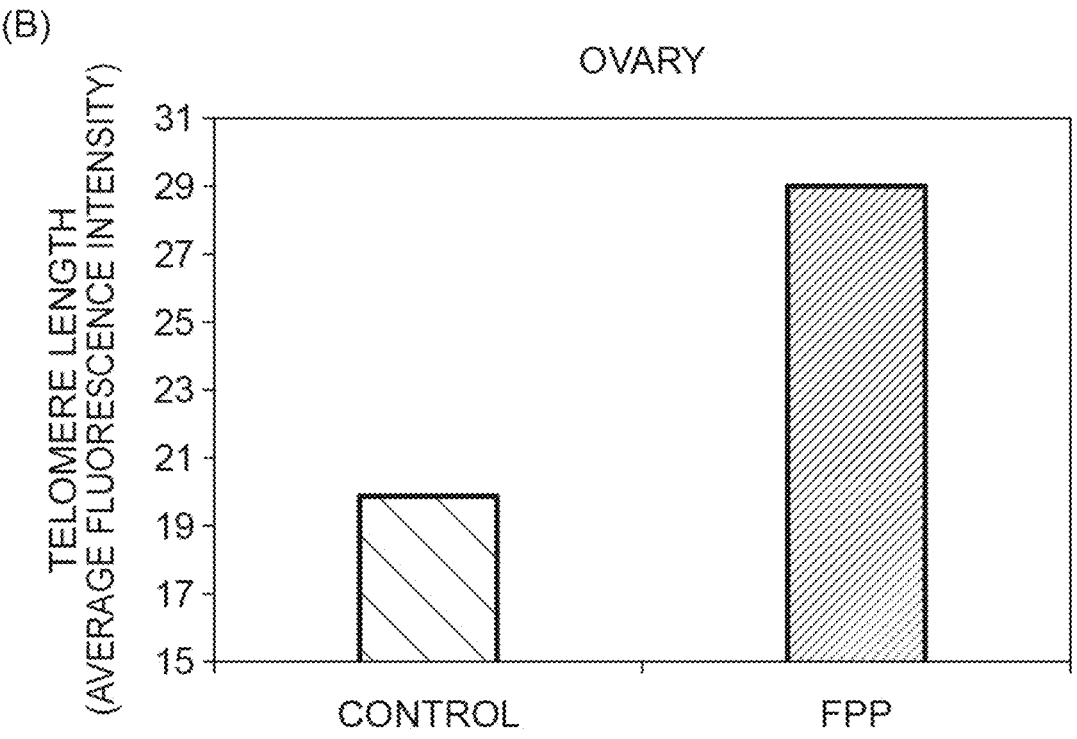

The measurement results of the telomere lengths of the bone marrow stem cells were shown in FIG. 2(A), and the measurement results of the telomere lengths of the ovarian germ cells were shown in FIG. 2(B). FIG. 2 has shown that the telomere length of the mice that ingested FPP was around three times the telomere length of the control mice, which did not ingest FPP, in both cells of the stem cells and the reproductive cells, at the end of the test (10 months).

These results have shown that FPP can induce antioxidant reaction, improve the telomerase activity, and increase the telomere length. This suggests that FPP improves a biological index related to aging apparently, and FPP can prevent aging. It can be estimated that FPP prolongates the reproductive period. Furthermore, the number of cells were counted using the above-mentioned prepared unicellular suspensions of the bone marrow and the ovaries, so that the number of cells in both organs of the mice that ingested FPP was around twice the number of cells of the control mice, which did not ingest FPP.

Example 2

First, 30 10-month-old female C57BL/6J mice (corresponding to humans at the age of around 50) were let to orally ingest an aqueous FPP solution everyday until the mice were 20 months old under the same conditions as in Example 1. Only tap water was given to a control group.

After the 10-month oral ingestion (20 months old), blood was collected. Experiments for confirming the telomerase activity, the total antioxidation ability, and the total gluta-thione in mouse plasma were performed. The telomerase activity and the total antioxidation ability were measured in the same way as in Example 1. The total glutathione was measured using a Glutathione Colorimetric Detection kit (Thermo Fisher Scientific K.K.) according to the instruc-tions.

Figure 3:
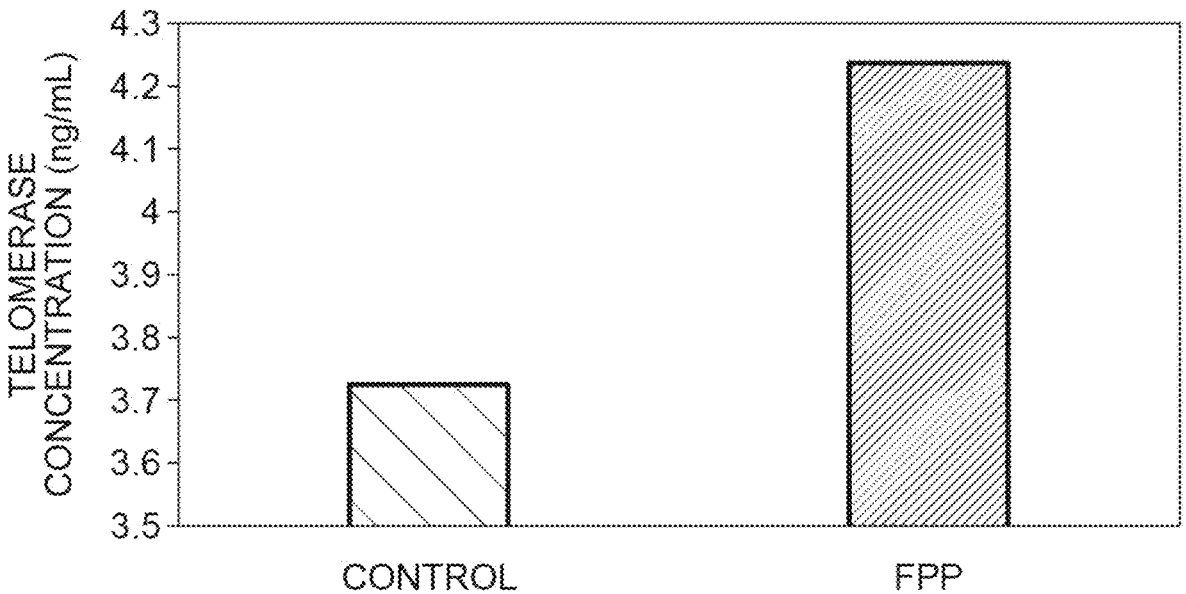
FIG. 3 shows the results of the telomerase activities in mouse plasma of Example 2.
Figure 4:
FIG. 4 shows the results of the total antioxidation abilities in mouse plasma of Example 2.
Figure 4:
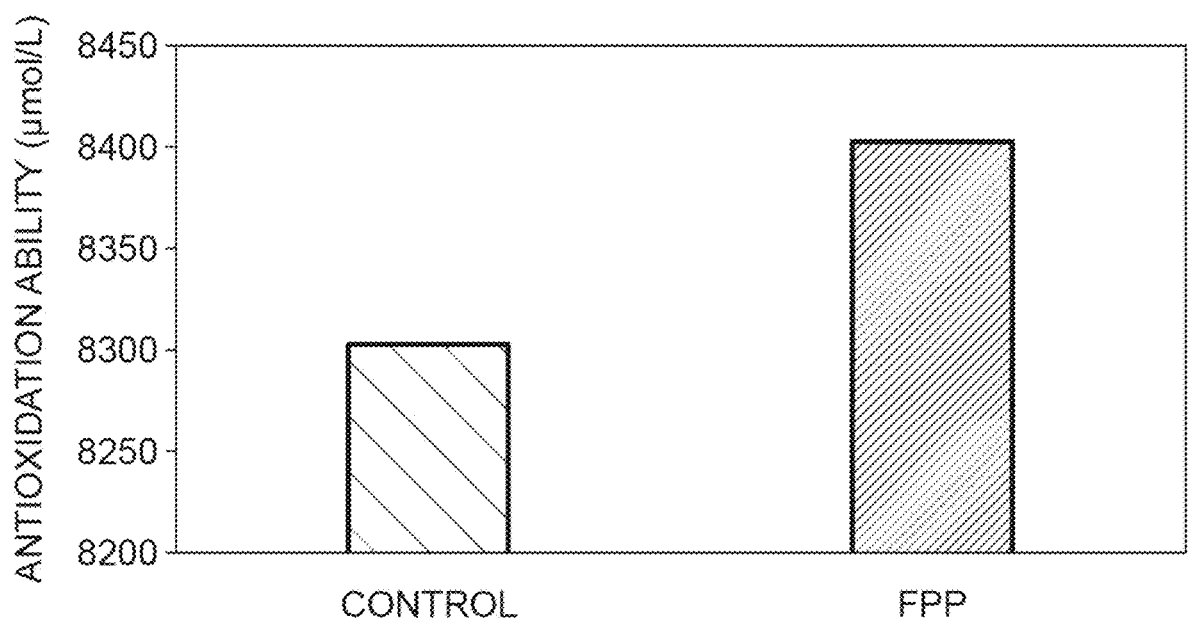
Figure 5:
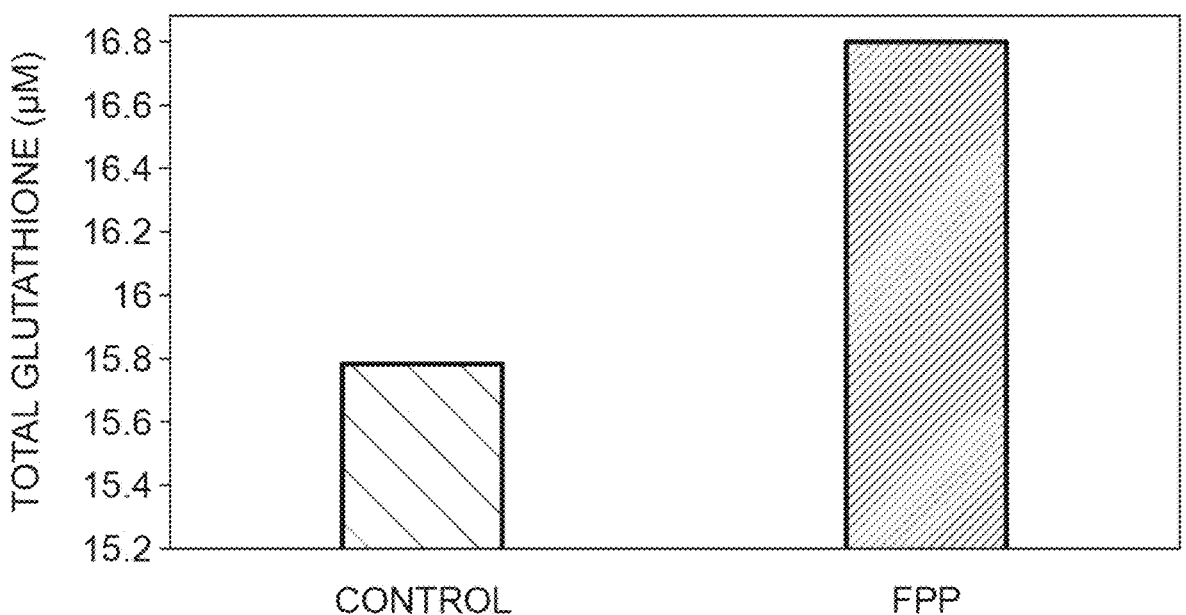
FIG. 5 shows the results of glutathione in mouse plasma of Example 2.

The measured values of the 30 mice were averaged. The results of the telomerase activities were shown in FIG. 3, the results of the total antioxidation abilities were shown in FIG. 4, and the results of the total glutathione were shown in FIG. 5. FIGS. 3 to 5 have shown that the telomerase activity, the total antioxidation ability, and the total glutathione in plasma of the mice that ingested FPP was around three times the telomerase activity, the total antioxidation ability, and the total glutathione in plasma of the control mice, which did not ingest FPP, at the end of the test. It has been proved that FPP also has an antiaging effect in aged mice. That is, it has been suggested that whether FPP is ingested from a young age or from an old age, an antiaging effect can be expected.

Example 3

(Experimental Material)

To obtain available cells from both bone marrow inde-pendent of sex, and ovaries dependent on sex, female mice (C57BL/6J) were used. All the experiments were approved by the ethics committee of Instituto Superiore di Sanitá (Italy, Rome) and implemented in accordance with Italian Law (Law 26/2014). Forty C57BL/6J female mice (16 to 20 g, 4 weeks old) were purchased from Charles River Labo-ratories Italia Srl (Calco, Lecco, Italy) and housed in animal facilities of Instituto Superiore di Smith. The mice were subjected to a light period for 10 hours and a dark period for 14 hours and let to ingest mouse diet (Mucedola Srl, Settimo Milanese (MI), Italy) and water freely.

(Experimental Method)

The mice were divided into two FPP ingestion groups (treated groups). In an FPP early treatment group (ET-FPP), FPP was administered to 6-week-old mice everyday for 10 months (6 weeks old to 51 weeks old). In an FPP late treatment group (LT-FPP), FPP was administered to 51-week-old mice everyday for 10 months (51 weeks old to 96 weeks old). When the ages of the mice were compared with the ages of humans, 6 to 51-week-old (early treatment group) mice corresponds to 13 to 41-year-old humans, and 51 to 96-week-old (late treatment group) mice corresponds to 41 to 63-year-old humans.

An aqueous solution in which 3 g of FPP (registered trademark, Osato Research Institute) was dissolved in 500 mL of tap water (6 g/L) is given to the mice in the two treatment groups in 1 mL that corresponded to 6 mg/mouse/day everyday for 10 months. Only tap water is given to the control group.

(Measurement of Telomerase Activity)

The mouse telomerase activity (telomerase concentration) was measured by calorimetric sandwich-ELISA assay. Plasma samples of mice immediately before slaughter were measured using a mouse TE (telomerase) ELISA kit (Elab-science®, Houston, TX, USA). The optical density was measured at $450\pm2$ nm.

(Collection of Bone Marrow Stem Cells from Mice)

Immediately after the control group and the ET-FPP and LT-FPP mice were slaughtered, bone marrow was obtained from both the shinbones and the thighbones of the mouse hind limbs. The bone marrow was then placed in a physi-ological saline solution (NaCl) and shattered with the smooth end of a 5 mL syringe plunger. Bone marrow cells were isolated using a Falcon® 100 μm cell strainer (Corning Incorporated, NY, USA) to obtain homogenous unicellular suspensions from the bone marrow. The unicellular suspen-sions were washed with PBS twice and immediately used for measuring the telomere lengths.

(Collection of Ovarian Germ Cells from Mice)

Immediately after the control group and the ET-FPP and LT-FPP mice were slaughtered, the ovaries were incised, placed in a physiological saline solution (NaCl) containing 1% trypsin and 0.1 μM EDTA, separated from the rest of the reproductive systems with a cutter and shattered with the smooth end of a 5 mL syringe plunger. Ovarian germ cells were isolated using a Falcon® 100 pm cell strainer (Corning Incorporated, NY, USA), and connective tissues and frag-ments were sedimented to obtain homogenous unicellular suspensions from the ovaries. The unicellular suspensions were washed with PBS twice and immediately used for measuring the telomere lengths.

(Measurement of the Telomere Lengths)

Immediately after the slaughter, telomeres in the above-mentioned bone marrow stem cells and ovarian germ cells (reproductive cells) of the control group and the ET-FPP and LT-FPP mice were detected. A Telomere PNA kit/FITC (Agilent Technologies, Inc., Santa Clara, CA, USA) for flow cytometry was used therefor. This kit enables the detection of telomeres in nucleated hematopoietic cells using fluores-cent in situ hybridization and a fluorescein binding peptide nucleic acid (PNA) probe. The PNA recognizes a repetitive 6-nucleotide sequence in telomeres (TTAGGG), and hybrid-izes with the repetitive sequence. The results were evaluated by flow cytometry using a light source excited at 488 nm.

(Statistical Analysis)

The result was reported as an average value±a standard error, and the calculation was performed using GraphPad Prism software (San Diego, Calif., USA). The Student's t-test was applied to analyze the results. The statistical significance was p<0.05.

(Results)

Results of ET-FPP

Figure 6:
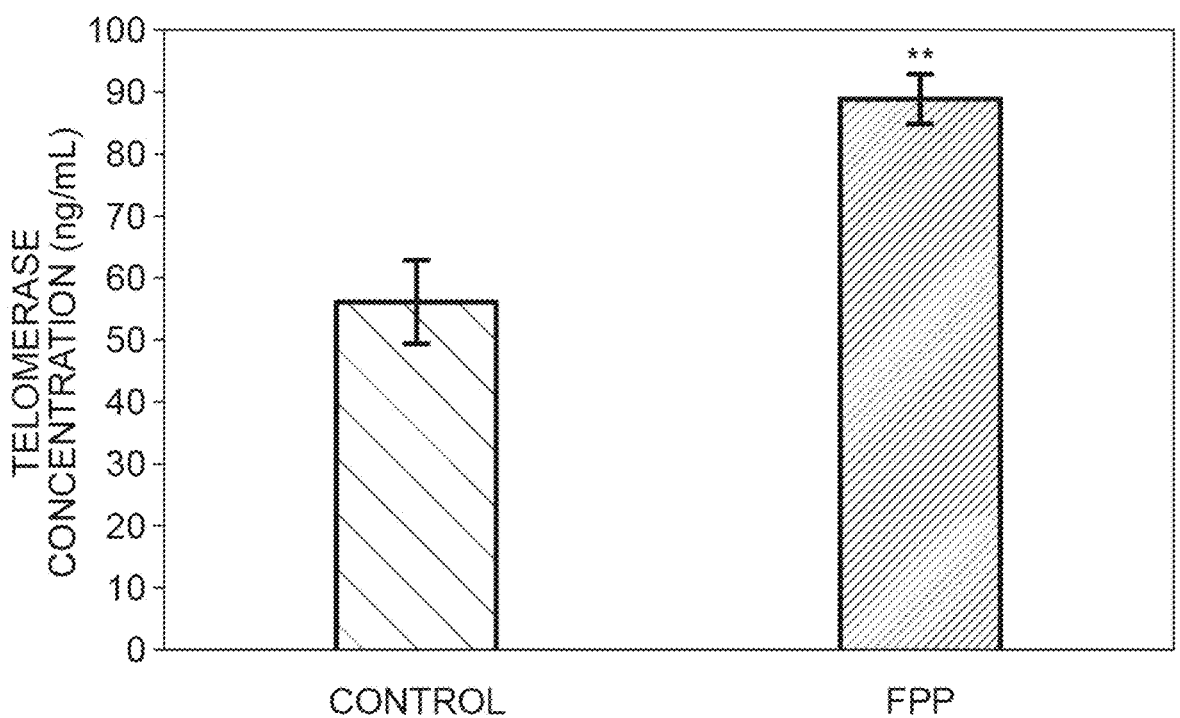
FIG. 6 shows the results of the telomerase activities of mice in the ET-FPP group of Examples 3 ($**p<0.005$).

The measurement results of the telomerase (TE) concen-trations in the plasma samples derived from the C57BL/6J female mice in the control group and the ET-FPP were shown in FIG. 6. An increase in the telomerase concentra-tion of the mice treated with FPP® everyday was confirmed as compared with the control group mice, which drank tap water. The ET-FPP mice specifically had a TE concentration 1.6 times higher (p<0.005) than the control group (ET-FPP: 88.5±4.5 ng/mL, control group: 55.9±6.6 ng/mL).

The unicellular suspensions were obtained from the bone marrow and the ovaries of the C57BL/6J female mice in the control group and ET-FPP as mentioned above. The unicel-lular suspensions of the bone marrow cells and the ovarian reproductive cells were counted under an optical microscope by trypan blue exclusion. The bone marrow cells and the ovarian reproductive cells in the ET-FPP mice was conse-quently around 4 times and twice more than the control cells, respectively (the data are not shown).

Figure 7:
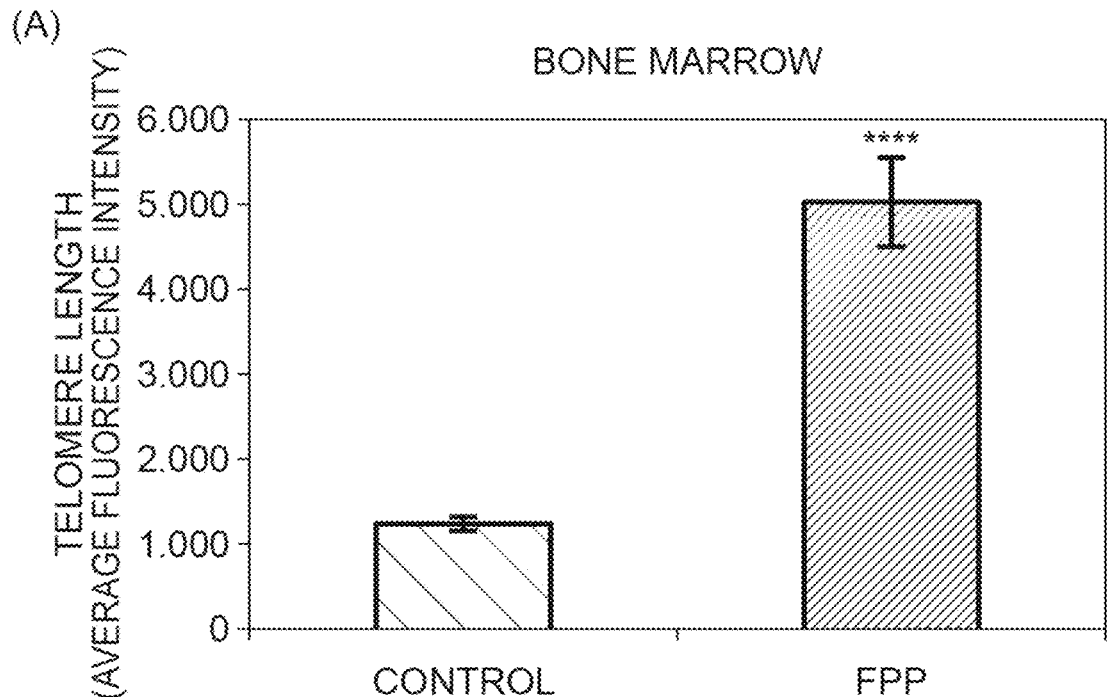
FIG. 7 shows the results obtained by measuring the telomere lengths of cells collected from mouse bone marrow (A) and the ovaries (B) of the ET-FPP group of Example 3 ($****p<0.0001$).
Figure 7:
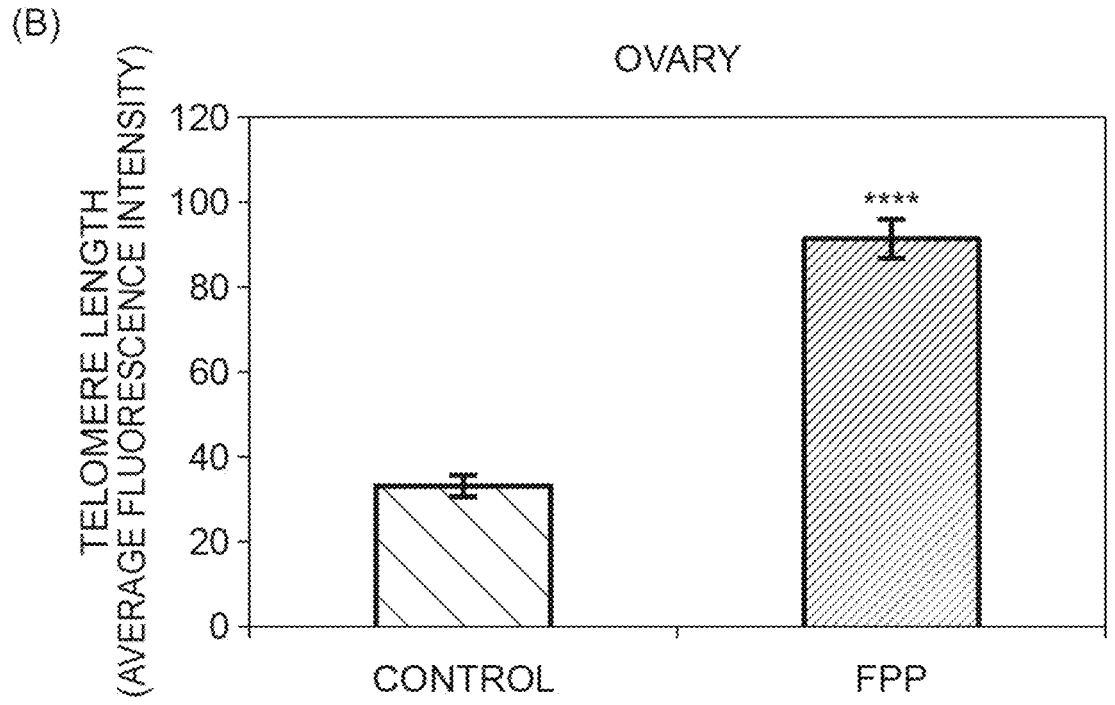

The telomere lengths of comparable numbers of bone marrow cells and ovarian reproductive cells were analyzed by hybridization with the fluorescein binding probe (PNA). The result of the average fluorescence intensity standardized with respect to all the cells and represented as an average±an SE is shown in FIG. 7. The TTAGGG sequence of the telomeres correlates with the value of the average fluores-cence intensity.

The results of FIG. 7 have shown that the ET-FPP mice exhibited significant increase in the telomere lengths in both the bone marrow (A) and the ovaries (B) as compared with the control group. The telomere length of the bone marrow cells was more specifically 4 times the length of the control group (ET-FPP: 5020±542 average fluorescence intensity, control group: 1228±88 average fluorescence intensity) (FIG. 7(A)), and the telomere length of the ovarian germ cells was 2.7 times the length of the control group (ET-FPP: 91±5 average fluorescence intensity, control group: 33±3 average fluorescence intensity) (FIG. 7(B)).

Results of LT-FPP

Figure 8:
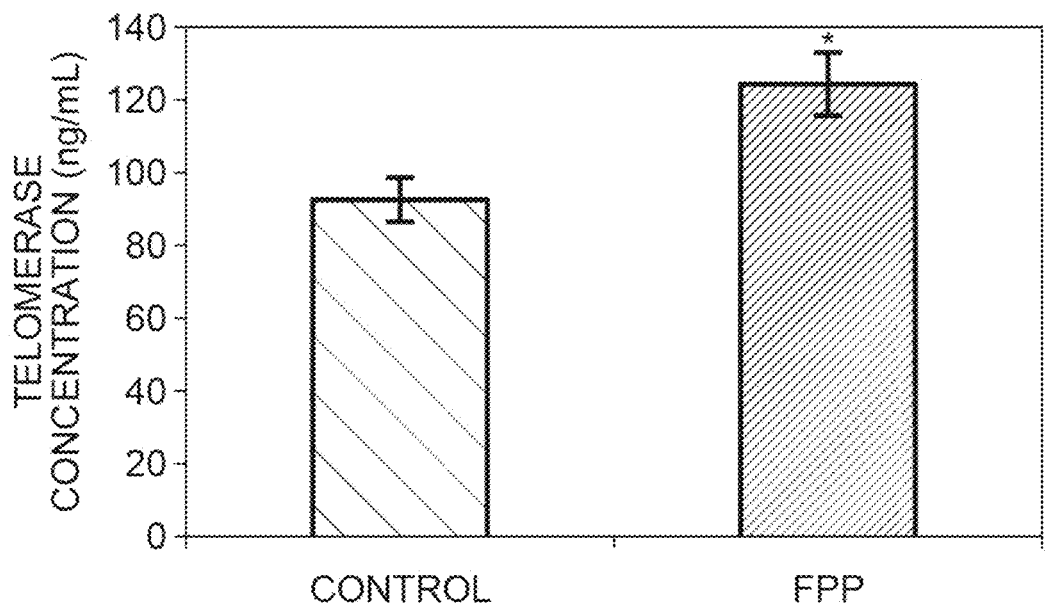
FIG. 8 shows the results of the telomerase activity of mice in the LT-FPP group of Example 3 ($*p<0.05$).

The measurement results of the telomerase (TE) concentrations in the plasma samples derived from the C57BL/6J female mice in the control group and the LT-FPP were shown in FIG. 8. An increase in the telomerase concentration of the mice treated with FPP® everyday was confirmed as compared with the control group mice, which drank tap water. The LT-FPP mice specifically had a TE concentration 1.6 times higher (p<0.005) than the control group (LT-FPP: 124.0±9.0 ng/mL, control: 92.5±6.5 ng/mL).

The unicellular suspensions were obtained from the bone marrow and the ovaries of the C57BL/6J female mice in the control group and LT-FPP as mentioned above. The unicellular suspensions of the bone marrow cells and the ovarian reproductive cells were counted under an optical microscope by trypan blue exclusion. The bone marrow cells and the ovarian reproductive cells in the LT-FPP mice was consequently around 1.8 times and twice more than the control cells, respectively (the data are not shown).

Figure 9:
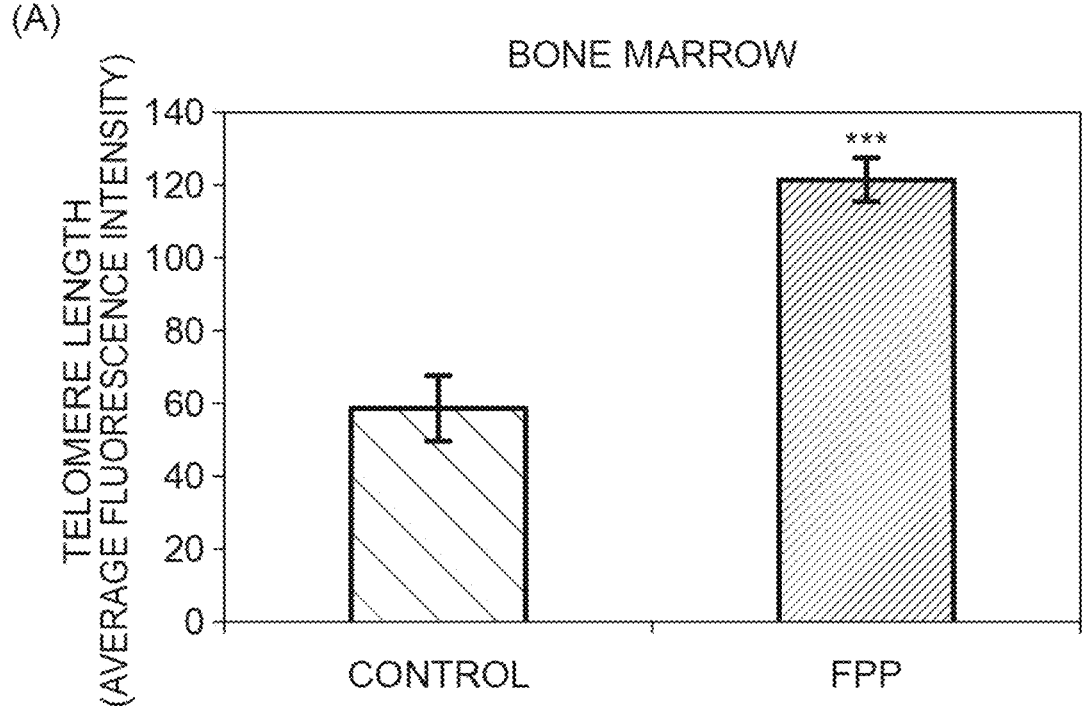
FIG. 9 shows the results obtained by measuring the telomere lengths of cells collected from mouse bone marrow (A) and the ovaries (B) of the LT-FPP group of Example 3 ($*p<0.05$, $***p<0.0005$).
Figure 9:
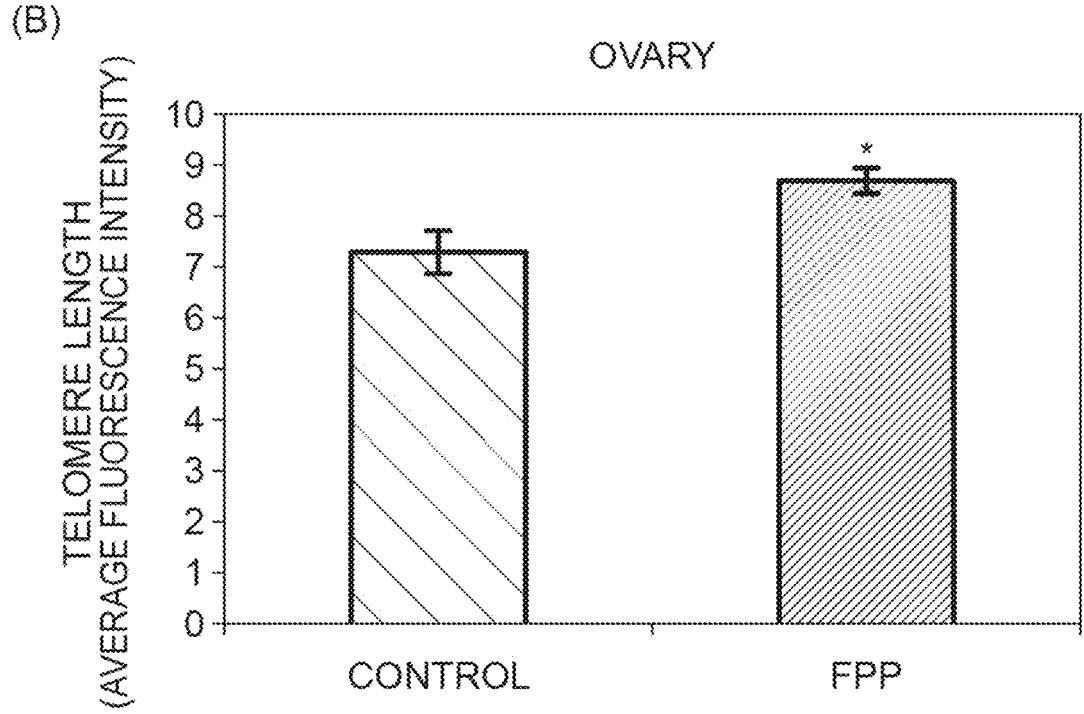

The telomere lengths of comparable numbers of bone marrow cells and ovarian reproductive cells were analyzed by hybridization with the fluorescein binding probe (PNA). The result of the average fluorescence intensity standardized with respect to all the cells and represented as an average±an SE is shown in FIG. 9. The TTAGGG sequence of the telomeres correlates with the value of the average fluorescence intensity.

The results of FIG. 9 have shown that the LT-FPP mice exhibited significant increase in the telomere lengths in both the bone marrow (A) and the ovaries (B) as compared with the control group. The telomere length of the bone marrow cells was more specifically twice the length of the control group (LT-FPP: 121±6 average fluorescence intensity, control group: 59±9 average fluorescence intensity) (FIG. 9(A)), and the telomere length of the ovarian germ cells was significantly longer than that of the control group (LT-FPP: 8.69±0.25 average fluorescence intensity, control group: 7.29±0.44 average fluorescence intensity) (FIG. 9(B)). The average fluorescence intensity in the bone marrow cells and the ovarian reproductive cells significantly decreased in the LT-FPP as compared with the ET-FPP.

The increase ratios (or decrease ratios) of the results in FPP-treated mice to the results in untreated (control) mice are shown in the following Table 1. The results of the antioxidation ability, the total glutathione, SOD-1, and the total reactive oxygen species (ROSs) are also shown besides telomerase and the telomere length. The values are values obtained by calculating the following: (FPP treatment–Control group)/Control group (%).

TABLE 1

| Comparison of ET-FPP with LT-FPP | | |
| --- | --- | --- |
| | ET-FPP | LT-FPP |
| Telomerase | +58% | +34% |
| Telomere length of bone marrow cells | +300% | +101% |
| Telomere length of ovarian germ cells | +174% | +19% |

10

TABLE 1-continued

| Comparison of ET-FPP with LT-FPP | | |
| --- | --- | --- |
| | ET-FPP | LT-FPP |
| Total antioxidation ability | +56% | +1% |
| Total glutathione | +640% | +34% |
| SOD-1 | +30% | +15% |
| Total ROS | −30% | −5% |

As shown in Table 1, the most useful effect was observed in the early treatment (ET-FPP). That is, it can be concluded that the early treatment with FPP from 6 weeks after birth was the most effective. It can be said that, in humans, the administration from the age of 13 is more effective.

INDUSTRIAL APPLICABILITY

Since fermented papaya preparation is highly safe, an antiaging effect is expected by daily ingestion. An antioxidation effect, improvement in reproductive ability, or the prolongation of reproductive periods can also be expected. The fermented papaya preparation can be utilized as a food composition or a pharmaceutical composition.

The invention claimed is:

1. A method of improving a reproductive ability in a patient in need thereof, comprising:
   orally administering an effective dose of fermented papaya preparation to the patient,
   wherein an effective dose is 0.5 to 6 g/day with respect to an adult having a body weight of 70 kg,
   the reproductive ability involves function of reproductive cells or germ cells, and
   the patient excludes a diabetic patient.

2. The method of claim 1, wherein the method further reduces telomere shortening due to aging.

3. The method of claim 1, wherein the method further improves telomerase activity.

4. The method according to claim 3, wherein the method further improves telomerase activity in reproductive cells or stem cells.

5. The method of claim 1, wherein the method further slows cell aging.

6. The method of claim 1, wherein the method further slows individual aging.

7. The method of claim 1, wherein the effective dosage is 3 to 6 g/day with respect to an adult having a body weight of 70 kg.

8. A method of prolonging a reproductive ability in a patient in need thereof, comprising:
   preparing a fermented papaya preparation by:
      fermenting immature fruit of Carica papaya Linn with sugar and/or edible yeast fungi, and
      adding a vehicle, a binder, or a lubricant to form the fermented papaya preparation in a form of granules, powder or fine granules, and
   administering an effective dose of the fermented papaya preparation to the patient,
   wherein the effective dose is 0.5 to 6 g/day with respect to an adult having a body weight of 70 kg,
   the reproductive ability involves function of reproductive cells or germ cells, and
   the patient excludes a diabetic patient.

9. The method of claim 8, wherein the method further reduces telomere shortening due to aging.

10. The method of claim 8, wherein the method further improves telomerase activity.

11

11. The method according to claim 8, wherein the method further improves telomerase activity in reproductive cells or stem cells.

12. The method of claim 8, wherein the method further slows cell aging.

13. The method of claim 8, wherein the method further slows individual aging.

14. The method of claim 1, wherein the method further elongates telomeres.

15. The method of claim 1, wherein the patient excludes a diabetic patient.

16. The method of claim 1, wherein the orally administering the effective dose of fermented papaya preparation starts when the patient is at an age of 13 to 60.

17. The method of claim 1, wherein the orally administering the effective dose of fermented papaya preparation starts when the patient is at an age of 15 or less.

18. The method of claim 1, wherein the orally administering the effective dose of fermented papaya preparation starts when the patient is at an age of 15 or more.

12

\* \* \* \* \*